US011370941B2

(12) United States Patent
Bhattacharyya et al.

(10) Patent No.: US 11,370,941 B2
(45) Date of Patent: Jun. 28, 2022

(54) METHODS AND SYSTEMS USING MOLECULAR GLUE FOR COVALENT BONDING OF SOLID SUBSTRATES

(71) Applicant: HI LLC, Los Angeles, CA (US)

(72) Inventors: Sukanta Bhattacharyya, Belmont, CA (US); Daniel Sobek, Portola Valley, CA (US)

(73) Assignee: HI LLC, Los Angeles, CA (US)

( * ) Notice: Subject to any disclaimer, the term of this patent is extended or adjusted under 35 U.S.C. 154(b) by 498 days.

(21) Appl. No.: 16/573,524

(22) Filed: Sep. 17, 2019

(65) Prior Publication Data
US 2020/0123416 A1 Apr. 23, 2020

Related U.S. Application Data

(60) Provisional application No. 62/798,330, filed on Jan. 29, 2019, provisional application No. 62/747,924, filed on Oct. 19, 2018.

(51) Int. Cl.
*C09J 5/06* (2006.01)
*C09J 185/00* (2006.01)
*C09J 183/16* (2006.01)
*G01R 33/12* (2006.01)
*A61B 5/245* (2021.01)
*C07F 7/08* (2006.01)

(52) U.S. Cl.
CPC ................ *C09J 5/06* (2013.01); *A61B 5/245* (2021.01); *C07F 7/081* (2013.01); *C09J 183/16* (2013.01); *C09J 185/00* (2013.01); *G01R 33/1284* (2013.01); *C09J 2400/126* (2013.01); *C09J 2400/146* (2013.01); *C09J 2483/00* (2013.01)

(58) Field of Classification Search
CPC ...... C09J 183/02; C09J 183/04; C09J 183/06; C09J 5/04; C09J 5/06; C07F 7/04
See application file for complete search history.

(56) References Cited

U.S. PATENT DOCUMENTS

| | | | |
|---|---|---|---|
| 4,951,674 A | 8/1990 | Zanakis et al. | |
| 5,030,699 A * | 7/1991 | Motoyama | C09D 183/04 528/33 |
| 5,181,417 A * | 1/1993 | Nishida | G01L 9/0042 73/114.18 |
| 5,189,368 A | 2/1993 | Chase | |
| 5,192,921 A | 3/1993 | Chantry et al. | |
| 5,254,947 A | 10/1993 | Chaillout et al. | |
| 5,309,095 A | 5/1994 | Ahonen et al. | |
| 5,442,289 A | 8/1995 | Dilorio et al. | |
| 5,444,372 A | 8/1995 | Wikswo, Jr. et al. | |
| 5,471,985 A | 12/1995 | Warden | |
| 5,506,200 A | 4/1996 | Hirschkoff et al. | |
| 5,526,811 A | 6/1996 | Lypchuk | |
| 5,713,354 A | 2/1998 | Warden | |
| 6,144,872 A | 11/2000 | Graetz | |
| 6,339,328 B1 | 1/2002 | Keene et al. | |
| 6,472,869 B1 | 10/2002 | Upschulte et al. | |
| 6,665,553 B2 | 12/2003 | Kandori et al. | |
| 6,806,784 B2 | 10/2004 | Hollberg et al. | |
| 6,831,522 B2 | 12/2004 | Kitching et al. | |
| 7,038,450 B2 | 5/2006 | Romalis et al. | |
| 7,102,451 B2 | 9/2006 | Happer et al. | |
| 7,145,333 B2 | 12/2006 | Romalis et al. | |
| 7,521,928 B2 | 4/2009 | Romalis | |
| 7,656,154 B2 | 2/2010 | Kawabata et al. | |
| 7,826,065 B1 | 11/2010 | Okandan et al. | |
| 7,872,473 B2 | 1/2011 | Kitching et al. | |
| 7,994,783 B2 | 8/2011 | Ledbetter et al. | |
| 8,054,074 B2 | 11/2011 | Ichihara et al. | |
| 8,212,556 B1 | 7/2012 | Schwindt et al. | |
| 8,258,884 B2 | 9/2012 | Borwick, III et al. | |
| 8,319,156 B2 | 11/2012 | Borwick, III et al. | |
| 8,334,690 B2 | 12/2012 | Kitching et al. | |
| 8,373,413 B2 | 2/2013 | Sugioka | |
| 8,405,389 B2 | 3/2013 | Sugioka et al. | |

(Continued)

FOREIGN PATENT DOCUMENTS

| | | |
|---|---|---|
| CN | 104730484 | 6/2015 |
| CN | 107562188 | 1/2018 |

(Continued)

OTHER PUBLICATIONS

Allred, J. C., Lyman, R. N., Kornack, T. W., & Romalis, M. V. (2002). High-sensitivity atomic magnetometer unaffected by spin-exchange relaxation. Physical review letters, 89(13), 130801.

Balabas et al. Polarized alkali vapor with minute-long transverse spin-relaxation time, Phys. Rev. Lett. 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Borna, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

(Continued)

*Primary Examiner* — Marc S Zimmer
(74) *Attorney, Agent, or Firm* — Branch Partners PLLC; Bruce E. Black

(57) ABSTRACT

A method for bonding together two substrates includes providing a molecular glue including glue molecules, each of the glue molecules having at least two —O—Si or —O—Al moieties; reacting a surface of a first substrate with the molecular glue to attach the glue molecules to the surface of the first substrate by at least one of the —O—Si or —O—Al moieties; and reacting a surface of a second substrate with the molecular glue to attach the glue molecules to the surface of the second substrate by at least another one of the —O—Si or —O—Al moieties. The method can be used for a variety of applications including manufacturing a vapor cell.

20 Claims, 3 Drawing Sheets

(56) References Cited

U.S. PATENT DOCUMENTS

| | | | |
|---|---|---|---|
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Kornack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Kornack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 10,024,929 B2 | 7/2018 | Parsa et al. |
| 10,088,535 B1 | 10/2018 | Shah |
| 10,162,016 B2 | 12/2018 | Gabrys et al. |
| 2004/0232912 A1 | 11/2004 | Tsukamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2006/0142146 A1* | 6/2006 | Gao .................. B01J 31/124 502/118 |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0079426 A1 | 3/2009 | Anderson |
| 2009/0101806 A1 | 4/2009 | Masuda |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0265042 A1 | 10/2013 | Kawabata et al. |
| 2014/0306700 A1 | 10/2014 | Kamada et al. |
| 2014/0354275 A1 | 12/2014 | Sheng et al. |
| 2015/0022200 A1 | 1/2015 | Ichihara et al. |
| 2015/0054504 A1 | 2/2015 | Ichihara et al. |
| 2015/0378316 A1 | 12/2015 | Parsa et al. |
| 2016/0061913 A1 | 3/2016 | Kobayashi et al. |
| 2016/0116553 A1 | 4/2016 | Kim et al. |
| 2016/0223627 A1 | 8/2016 | Shah et al. |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0199138 A1 | 7/2017 | Parsa et al. |
| 2017/0261564 A1 | 9/2017 | Gabrys et al. |
| 2017/0331485 A1 | 11/2017 | Gobet et al. |
| 2017/0343617 A1 | 11/2017 | Manickam et al. |
| 2017/0343695 A1 | 11/2017 | Stetson et al. |
| 2018/0003777 A1 | 1/2018 | Sorenson et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |

FOREIGN PATENT DOCUMENTS

| | | | |
|---|---|---|---|
| EP | 2738627 A3 | 6/2014 |
| EP | 2385028 B1 | 10/2015 |
| EP | 3037836 B1 | 9/2017 |
| JP | 2004-307655 A | * 11/2004 |
| JP | 2009-299042 A | * 12/2009 |
| JP | 2016109665 | 6/2016 |
| JP | 2018004462 | 1/2018 |
| WO | 2005/081794 | 9/2005 |
| WO | 2014/031985 | 2/2014 |
| WO | 2017/095998 | 6/2017 |

OTHER PUBLICATIONS

Dang, H.B. & Maloof, A.C. & Romalis, Michael. (2009). Ultra-high sensitivity magnetic field and magnetization measurements with an atomic magnetometer. Applied Physics Letters. 97. 10.1063/1.3491215.

Donley, E.A. & Hodby, E & Hollberg, L & Kitching, J. (2007). Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (10).ISSN 2331-7019.

Jiménez-Martínez, R., Griffith, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.

Kiwoong Kim, Samo Begus, Hui Xia, Seung-Kyun Lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi:10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84. 10.1103/PhysRevA.84.061403.

Maze, J. R., Stanwix, P. L., Hodges, J. S., Hong, S., Taylor, J. M., Cappellaro, P., . . . & Yacoby A. (2008). Nanoscale magnetic sensing with an individual electronic spin in diamond. Nature, 455(7213), 644.

(56) References Cited

OTHER PUBLICATIONS

Sander TH, Preusser J, Mhaskar R, Kitching J, Trahms L, Knappe S. Magnetoencephalography with a chip-scale atomic magnetometer. Biomed Opt Express. 2012;3(5):981-90.
J. Seltzer, S & Romalis, Michael. (2010). High-temperature alkali vapor cells with antirelaxation surface coatings. Journal of Applied Physics. 106. 114905-114905. 10.1063/1.3236649.
Seltzer, S. J., and Romalis, M.V., "Unshielded three-axis vector operation of a spin-exchange-relaxation-free atomic magnetometer." Applied physics letters 85.20 (2004): 4804-4806.
Sheng, Dang & R. Perry, Abigail & Krzyzewski, Sean & Geller, Shawn & Kitching, John & Knappe, Svenja. (2017). A microfabricated optically-pumped magnetic gradiometer. Applied Physics Letters. 110. 10.1063/1.4974349.
Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.
Volkmar Schultze et al. An Optically Pumped Magnetometer Working in the Light-Shift Dispersed Mz Mode, Sensors 2017, 17, 561; doi:10.3390/s17030561.
Fang, J. and Qin, J., 2012. In situ triaxial magnetic field compensation for the spin-exchange-relaxation-free atomic magnetometer. Review of Scientific Instruments, 83(10), p. 103104.
Joon Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.
Griffith, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.
Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.
Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.
Kim, Young Jin & Savukov, I. (2016). Ultra-sensitive Magnetic Microscopy with an Optically Pumped Magnetometer, Scientific Reports. 6. 24773. 10.1038/srep24773.
Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.
Orang Alem, Rahul Mhaskar, Ricardo Jiménez-Martínez, Dong Sheng, John LeBlanc, Lutz Trahms. Tilmann Sander, John Kitching, and Svenja Knappe, "Magnetic field imaging with microfabricated optically-pumped magnetometers," Opt. Express 25, 7849-7858 (2017).
Slocum et al., Self-Calibrating Vector Magnetometer for Space, https://esto.nasa.gov/conferences/estc-2002/Papers/B3P4(Slocum).pdf.
Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639. 10.1016/0375-9601(69) 90480-0.
J. A. Neuman, P. Wang, and A. Gallagher, Robust high-temperature sapphire cell for metal vapors, Review of Scientific Instruments, vol. 66, Issue 4, Apr. 1995, pp. 3021-3023.
Borna, Amir, et al. "A 20-channel magnetoencephalography system based on optically pumped magnetometers." Physics in Medicine & Biology 62.23 (2017): 8909.
R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.
Hu, Yanhui & Hu, Zhaohul & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/AO.56.005927.
Masuda, Y & Ino, T & Skoy, Vadim & Jones, G.L. (2005). 3He polarization via optical pumping in a birefringent cell. Applied Physics Letters. 87. 10.1063/1.2008370.
A.B. Baranga et al., An atomic magnetometer for brain activity imaging, Real Time Conference 2005. 14th IEEE—NPSS. pp. 417-418.
Larry J. Ryan, Robert E. Slocum, and Robert B. Steves, Miniature Vector Laser Magnetometer Measurements of Earth's Field, May 10, 2004, 4 pgs.
Lorenz, V. O., Dai, X., Green, H., Asnicar, T. R., & Cundiff, S. T. (2008). High-density, high-temperature alkali vapor cell. Review of Scientific Instruments, 79(12), 4 pages.
F. Jackson Kimball, D & Dudley, J & Li, Y & Thulasi, Swecha & Pustelny, Szymon & Budker, Dmitry & Zolotarev, Max. (2016). Magnetic shielding and exotic spin-dependent interactions. Physical Review D. 94. 10.1103/PhysRevD.94.082005.
Huang, Haichao, et al. "Single-beam three-axis atomic magnetometer." Applied Physics Letters 109.6 (2016): 062404. (Year: 2016).
Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.
Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.
S. Knappe, V. Shah, P. Schwindt, L. Hollberg, J. Kitching, L. Liew, and J. Moreland. A microfabricated atomic clock. Applied Physics Letters, 85(9):1460-1462, 2004.
L. Nieradko, C. Gorecki, A. Douahi, V. Giordano, J.-C. Beugnot, J. Dziuban, and M. Moraja. New approach of fabrication and dispensing of micromachined cesium vapor cell. Journal of Micro/Nanolithography, MEMS, and MOEMS, 7(3):033013, 2008.
V. Maurice, J. Rutkowski, E. Kroemer, S. Bargiel, N. Passilly, R. Boudot, C. Gorecki, L. Mauri, and M. Moraja. Microfabricated vapor cells filled with a cesium dispensing paste for miniature atomic clocks. Applied Physics Letters, 110(16):164103, 2017.
V. Maurice, J. Rutkowski, E. Kroemer, S. Bargiel, N. Passilly, R. Boudot, R. Chutani, S. Galliou, and C. Gorecki. Microfabricated vapor cells for miniature atomic clocks based on post-sealing activated cesium dispensers. In International Frequency Control Symposium (IFCS), Joint with the 31st European Frequency and Time Forum (EFTF), pp. 636-637, Besançon, France, 2017.
F. Gong, Y. Jau, K. Jensen, and W. Happer. Electrolytic fabrication of atomic clock cells. Review of Scientific Instruments, 77(7):711-714, 2006.
M. Bick, H. Prinz, and A. Steinmetz. Ullmann's Encyclopedia of Industrial Chemistry, chapter Cesium and Cesium Compounds. Wiley Online Library, 2000.
L. Liew, S. Knappe, J. Moreland, H. Robinson, L. Hollberg, and J. Kitching. Microfabricated alkali atom vapor cells. Applied Physics Letters, 84(14):2694-2696, 2004.
L. Liew, J. Moreland, and V. Gerginov. Wafer-level filling of microfabricated atomic vapor cells based on thin-film deposition and photolysis of cesium azide. Applied Physics Letters, 90(11):114106, 2007.
S. Woetzel, V. Schultze, R. IJsselsteijn, T. Schulz, S. Anders, R. Stolz, and H. Meyer. Microfabricated atomic vapor cell arrays for magnetic field measurements. Review of Scientific Instruments, 82(3):033111, 2011.
W. Wei, J. Shang, W. Kuai, S. Qin, T. Wang, and J. Chen. Fabrication of wafer-level spherical Rb vapor cells for miniaturized atomic clocks by a chemical foaming process. In 13th International

(56) References Cited

OTHER PUBLICATIONS

Conference on Electronic Packaging Technology & High Density Packaging (ICEPTHDP), pp. 1639-1641, Guilin, Guangxi, China, 2012.

Larry J. Ryan, Robert E. Slocum, and Robert B. Steves; Miniature Vector Laser Magnetometer Measurements of Earth's Field; Polatomic, Inc.; May 10, 2004; 4 pages.

S. Theppakuttai, D. Shao, and S. Chen. Localized Laser Transmission Bonding for Microsystem Fabrication and Packaging. Journal of Manufacturing Processes, 6(1):24-31, 2004.

Evangelina Pensa, Emiliano Cortés, Gastón Corthey, Pilar Carro, Carolina Vericat, Mariano H. Fonticelli, Guillermo Benítez, Aldo A. Rubert, and Roberto C. Salvarezza; The Chemistry of the Sulfur-Gold Interface: In Search of a Unified Model; Accounts of Chemical Research 2012 45 (8), 1183-1192.

Helmut Hinterwirth, Stefanie Kappel, Thomas Waitz, Thomas Prohaska, Wolfgang Lindner, and Michael Lämmerhofer; Quantifying Thiol Ligand Density of Self-Assembled Monolayers on Gold Nanoparticles by Inductively Coupled Plasma-Mass Spectrometry; ACS Nano 2013 7 (2), 1129-1136.

Sasan Asiaei, Patricia Nieva, and Mathilakath M. Vijayan; Fast Kinetics of Thiolic Self-Assembled Monolayer Adsorption on Gold: Modeling and Confirmation by Protein Binding; The Journal of Physical Chemistry B 2014 118 (47), 13697-13703.

Dong Yan, Jeremy A. Saunders, and, and G. Kane Jennings; Kinetics of Formation for n-Alkanethiolate Self-Assembled Monolayers onto Gold in Aqueous Micellar Solutions of C12E6 and C12E7; Langmuir 2002 18 (26), 10202-10212.

Sahoo, H. K., Ottaviano, L., Zheng, Y., Hansen, O., & Yvind, K. (2018). Low temperature bonding of heterogeneous materials using Al2O3 as an intermediate layer. In Proceedings of SPIE (vol. 10535). [105350V] SPIE—International Society for Optical Engineering. (Proceedings of S P I E—International Society for Optical Engineering). DOI: 10.1117/12.2289526.

Douglas, R., van Veggel, A. A., Cunningham, L., Haughian, K., Hough, J., & Rowan, S. (2014). Cryogenic and room temperature strength of sapphire jointed by hydroxide-catalysis bonding. Class. Quantum Grav. 31 (2014) DOI: 10.1088/0264-9381/31/4/045001.

Syvain Karlen—Doctorate Thesis—"Fabrication and characterization of MEMS alkali vapor cells used in chip-scale atomic clocks and other atomic devices"—University of Neuchatel—Dec. 2017. (Relevant pp. Chapter 3 44-48).

A. Pelton. The Ca—Rb (Calcium-Rubidium) system. Bulletin of Alloy Phase Diagrams, 6(1):37, 1985.

Abstract for C.-H Lee, H. Guo, S. Radhakrishnam, A. Lal, C. Szekely, T. McClellan, and A. Pisano. A batch fabricated rubidium-vapor resonance cell for chip-scale atomic clocks. In Solid-State Sensors, Actuators and Microsystems Workshop, Hilton Head Island, SC, United States, 2005. (Abstract only found at https://www.jstage.jst.go.jp/article/ieejsmas/131/7/131_7_251/_article/-char/ja/).

* cited by examiner

METHODS AND SYSTEMS USING MOLECULAR GLUE FOR COVALENT BONDING OF SOLID SUBSTRATES

CROSS-REFERENCE TO RELATED APPLICATIONS

This application claims the benefit of U.S. Provisional Patent Applications Ser. Nos. 62/747,924, filed Oct. 19, 2018, and 62/798,330, filed Jan. 29, 2019, which are incorporated herein by reference in their entireties.

FIELD

The present disclosure is directed to the area of solid substrate bonding. The present disclosure is also directed to methods and systems for bonding solid substrates, as well as the articles or devices that include the bonded solid substrates.

BACKGROUND

In semiconductor processes, particularly for Microfabricated Electro-Mechanical Systems (MEMS), wafer substrates can be bonded together as part of the manufacture of devices. In many instances, the bonding is performed using anodic bonding (e.g., silicon to glass) or fusion bonding (glass-to-glass or sapphire-to-sapphire) techniques. The development of precision covalent binding techniques for sapphire and related materials, such as corundum, is useful for engineering advanced devices. Many conventional methods utilize bases, such as NaOH and KOH, under aqueous conditions which may not be suitable for at least some applications.

BRIEF SUMMARY

One embodiment is a method for bonding together two substrates. The method includes providing a molecular glue including glue molecules, each of the glue molecules having at least two —O—Si or —O—Al moieties; reacting a surface of a first substrate with the molecular glue to attach the glue molecules to the surface of the first substrate by at least one of the —O—Si or —O—Al moieties; and reacting a surface of a second substrate with the molecular glue to attach the glue molecules to the surface of the second substrate by at least another one of the —O—Si or —O—Al moieties.

In at least some embodiments, the glue molecules are selected from $Al(OR)_3$ or $Si(OR)_4$, wherein each R is independently hydrogen or $C_1$ to $C_8$ branched or unbranched alkyl. In at least some embodiments, each R is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, or —$C(CH_3)_3$.

In at least some embodiments, the glue molecules each contain two or more aluminum or silicon atoms. In at least some embodiments, the glue molecules are selected from $Al(OR)_2$—O-L-O—$Al(OR)_2$ or $Si(OR)_3$—O-L-O—$Si(OR)_3$, wherein each R is independently hydrogen or $C_1$ to $C_8$ branched or unbranched alkyl and L is a linker group selected from $C_1$ to $C_{30}$ branched or unbranched alkylene or $C_6$ to $C_{30}$ cycloalkylene or $C_6$ to $C_{30}$ arylene. In at least some embodiments, each R is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, or —$C(CH_3)_3$. In at least some embodiments, L is —$(CH_2)_x$— or benzylene, wherein x is an integer in the range of 1 to 15.

In at least some embodiments, at least one of the first substrate or the second substrate is an inorganic substrate. In at least some embodiments, at least one of the first substrate or the second substrate is a silicon, glass, aluminum oxide, corundum, ruby, or sapphire substrate. In at least some embodiments, both the first and second substrates are silicon, glass, aluminum oxide, corundum, ruby, or sapphire substrates.

In at least some embodiments, reacting the surface of the first substrate with the molecular glue includes disposing the molecular glue on the surface and applying heat or pressure or both heat and pressure to react the molecular glue with the surface. In at least some embodiments, reacting the surface of the first substrate with the molecular glue and reacting the surface of the second substrate with the molecular glue include disposing the molecular glue on the surface of the first substrate, positioning the second substrate on the first substrate, and applying heat or pressure or both heat and pressure to react the molecular glue with the surfaces of the first and second substrates.

Another embodiment is a method for forming a vapor cell. The method includes providing a molecular glue including glue molecules, each of the glue molecules having at least two —O—Si or —O—Al moieties; reacting a surface of a first vapor cell substrate with the molecular glue to attach the glue molecules to the surface of the first vapor cell substrate by at least one of the —O—Si or —O—Al moieties; and reacting a surface of a second vapor cell substrate with the molecular glue to attach the glue molecules to the surface of the second vapor cell substrate by at least another one of the —O—Si or —O—Al moieties.

In at least some embodiments, the first vapor cell substrate is a first cell wall and the second vapor cell substrate is a second cell wall. In at least some embodiments, the first vapor cell substrate is a cell wall and the second vapor cell substrate is an optical component of the vapor cell. In at least some embodiments, the first vapor cell substrate is a first optical component and the second vapor cell substrate is a second optical component. In at least some embodiments, the first optical component is selected from a collimating element, a quarter wave plate, or a lens element.

Yet another embodiment is a vapor cell that includes a first substrate forming either a first cell wall or a first optical component; a second substrate forming either a second cell wall or a second optical component; and a molecular glue disposed between the first and second substrates and bonding the first and second substrates together, wherein a molecular glue includes glue molecules, each of the glue molecules including at least two —O—Si or —O—Al moieties, wherein the —O—Si or —O—Al moieties form silicate or aluminate bonds to the first and second substrates.

In at least some embodiments, the glue molecules are selected from $Al(OR)_3$ or $Si(OR)_4$, wherein each R is independently hydrogen or $C_1$ to $C_8$ branched or unbranched alkyl. In at least some embodiments, the glue molecules are selected from $Al(OR)_2$—O-L-O—$Al(OR)_2$ or $Si(OR)_3$—O-L-O—$Si(OR)_3$, wherein each R is independently hydrogen or $C_1$ to $C_8$ branched or unbranched alkyl and L is a linker group selected from $C_1$ to $C_{30}$ branched or unbranched alkylene or $C_6$ to $C_{30}$ cycloalkylene or $C_6$ to $C_{30}$ arylene.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
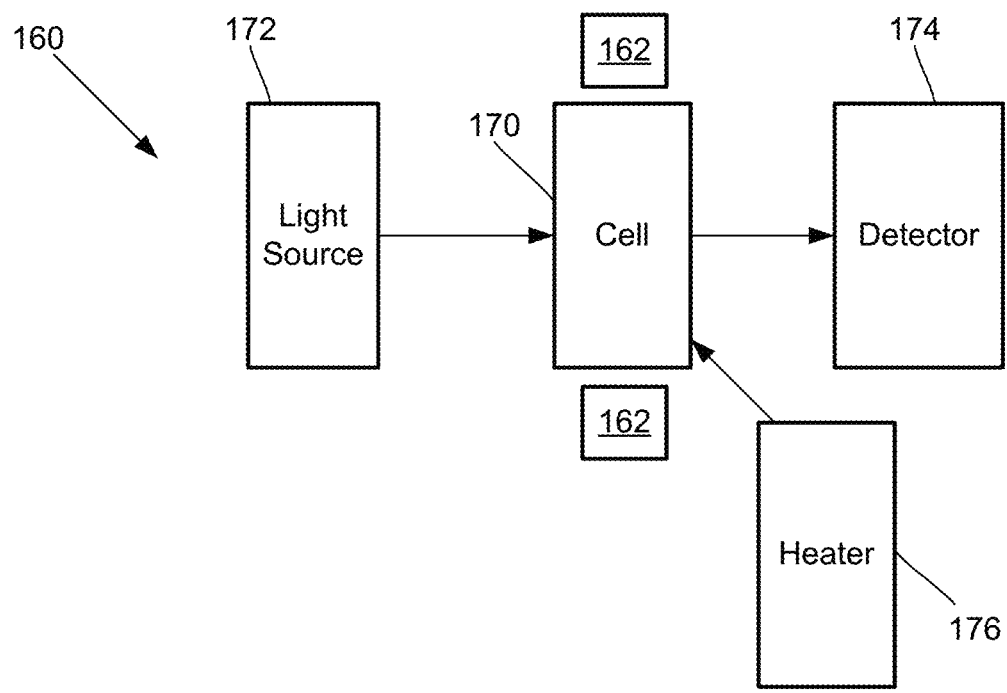
FIG. 1A is a schematic block diagram of one embodiment of a magnetometer, according to the invention.

The present disclosure is directed to the area of solid substrate bonding. The present disclosure is also directed to methods and systems for bonding solid substrates, as well as the articles or devices that include the bonded solid substrates.

In contrast to conventional anodic or fusion bonding techniques, a molecular glue can be used to bond two solid substrates together. As an example, the molecular glue, as described herein, is suitable for bonding two inorganic substrates, such as silicon, glass, or aluminum oxide substrates including corundum, ruby, and sapphire substrates. The two substrates may be made of the same material or may be made of different materials. For example, the molecular glue can be used to bond a sapphire substrate to another sapphire substrate or to a glass or silicon substrate. It will be recognized that the molecular glues described herein can be used with substrates other than sapphire, glass, or silicon.

Molecular glues include glue molecules that are a class of bi-functional linkers capable of covalently binding two components together. A molecular glue, as defined herein, includes glue molecules having at least one or two silicon or aluminum atoms, or any combination thereof. In at least some embodiments, the glue molecules have at least two bonding moieties such as —O—Si or —O—Al moieties. In at least some embodiments, each silicon or aluminum atom of a glue molecule is part of two or more of the —O—Si or —O—Al moieties. In at least some embodiments with two silicon or aluminum atoms, the silicon or aluminum atoms are coupled together by an organic linker. In at least some embodiments, the silicon and aluminum atoms form covalent silicate or aluminate bonds with the substrates.

In some embodiments, the glue molecules of a molecular glue are all the same. In other embodiments, a molecular glue may be composed of two or more different glue molecules.

Examples of glue molecules include, but at not limited to, $Al(OR)_3$ (with three —O—Al moieties), $Si(OR)_4$ (with four —O—Si moieties), $Al(OR)_2$—O-L-O—$Al(OR)_2$ (with four —O—Al moieties), or $Si(OR)_3$—O-L-O—$Si(OR)_3$ (with six —O—Al moieties). Each R is independently hydrogen or a $C_1$ to $C_8$ branched or unbranched alkyl which may be substituted or unsubstituted. The R groups can be substituted with one or more alkenyl, alkynyl, cycloalkyl (including cycloalkyl groups two or more rings), or aryl (including aryl groups with two or more fused or unfused rings) substituents. Preferably, any substituent of the R groups does not react with the substrate or substantially hinder the bonding of the glue molecule to the substrate. In at least some embodiments, the R groups of the glue molecules are the same. In other embodiments, the R groups of the glue molecules may be different. In at least some embodiments, the R groups are each independently hydrogen or an unsubstituted branched or unbranched alkyl such as, for example, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, or —$C(CH_3)_3$.

L is a linker group which, in at least some embodiments, is a $C_1$ to $C_{30}$ branched or unbranched alkylene or $C_6$ to $C_{30}$ cycloalkylene (including cycloalkylene with two or more rings) or $C_6$ to $C_{ao}$ arylene (including arylene with two or more fused or unfused rings), any of which may be substituted or unsubstituted and may include one or more oxygen, nitrogen, or other heteroatoms. The L group can be substituted with one or more alkenyl, alkynyl, cycloalkyl, or aryl substituents. In at least some embodiments, L is —$(CH_2)_x$— or benzylene where x is an integer in the range of 1 to 15.

Examples of suitable compounds for molecular glues include, but are not limited to, the following:

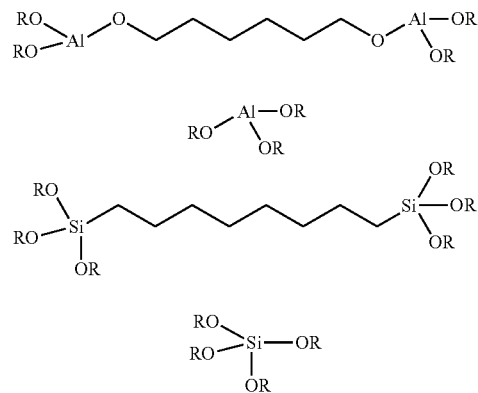

as well as 1,2-Bis(triethoxysilyl)ethane and 1,4-Bis(triethoxysilyl)benzene, where the R groups are defined above and may be, for example, independently H, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, or —$C(CH_3)_3$. In at least some embodiments, the R groups of the glue molecules are the same. In other embodiments, the R groups of the glue molecules may be different.

An example of sapphire bonding using a molecular glue (in this example, bis-aluminum glue molecules) is illustrated in the equations below:

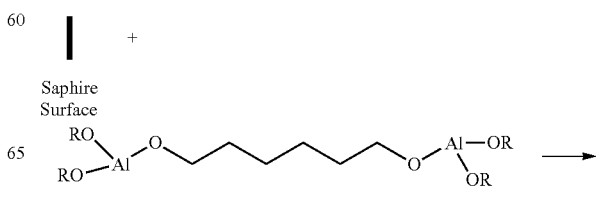

-continued

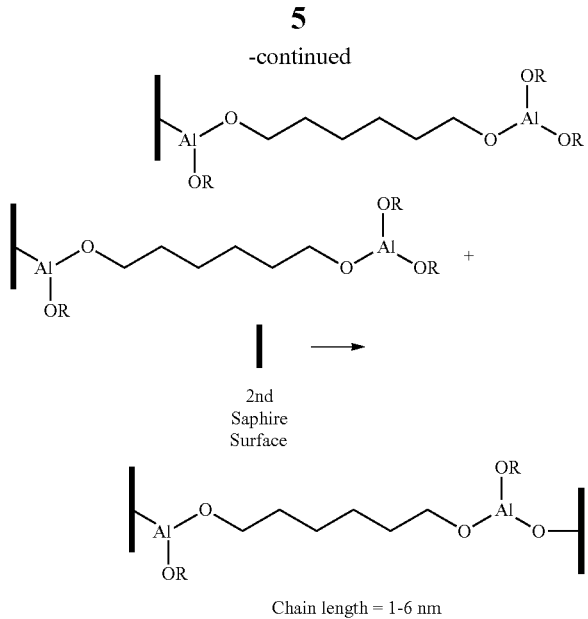

Chain length = 1-6 nm

The following is an example of one embodiment of a method of bonding sapphire substrates using a molecular glue. The substrates are sapphire wafers. The wafers are prepared by piranha etch to remove any residual organic residue on the substrates. The wafers are then dried. The molecular glue is spin coated on an unpatterned surface of one of the sapphire wafers. The wafers are then dried again. The wafers are brought into contact with each other and flat aligned. Pressure and temperature are applied to react the molecular glue with the two wafers and bond the wafers together. In at least some embodiments, this step may be performed in a wafer bonder at a given pressure within equipment limits and, at least in some embodiments, temperature not to exceed 100 degrees Celsius.

Other methods of bonding substrates using the molecular glue can be utilized. For example, the molecular glue can be applied to the substrates using any suitable method including, but not limited to, spin coating, dip coating, spray coating, roll coating, knife coating, silk screening, or any other suitable coating method. The molecular glue can be reacted with the substrates using any suitable technique or combination of techniques including, but not limited to, thermal activation, pressure activation, light or ultraviolet activation, or the like or any combination thereof.

In at least some embodiments, the molecular glues and techniques described herein can provide a simple method for wafer bonding that does not require temperatures above 100 degrees Celsius. In at least some embodiments, these techniques can be less sensitive to surface roughness of the substrate that conventional bonding methods. In at least some embodiments, the covalent bonding reaction of the molecular glue to the substrate does not produce water as a side-product.

In at least some embodiments, the methods and techniques described herein can have one or more of the following advantages over conventional bonding methods: 1) more binding sites and stronger bonding, as the glue molecules are used as a limiting reagent; 2) low temperature bonding (for example, the bonding reaction occurs at a temperature of 100, 90, 80, 75, or 50 degrees Celsius or less); 3) water is not a reaction product (which may be beneficial for vapor cells that house alkali metals, as described below); 4) neutral, non-aqueous reaction conditions; 5) allows binding of two heterogeneous materials; and 6) linker length may be fine-tuned depending on, for example, substrate surface roughness.

The molecular glue described above can be utilized in a number of different applications. For example, the molecular glue can be utilized in manufacturing a vapor cell (or gas cell) or a magnetometer (such as an optically pumped magnetometer) that includes a vapor cell (or gas cell).

FIG. 1A is a schematic block diagram of one embodiment of a magnetometer 160 which includes a vapor cell 170 (also referred to as a "cell") such as an alkali metal vapor cell; a heating device 176 to heat the cell 170; a light source 172; and a detector 174. In addition, coils of a magnetic field generator 162 can be positioned around the vapor cell 170. The vapor cell 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) and a buffer gas (for example, nitrogen, helium, neon, or argon). In some embodiments, the vapor cell may include the alkali metal atoms in a prevaporized form prior to heating to generate the vapor.

The light source 172 can include, for example, a laser to, respectively, optically pump the alkali metal atoms and probe the gas cell. The light source 172 may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source 172 may include two light sources: a pump light source and a probe light source.

The detector 174 can include, for example, an optical detector to measure the optical properties of the transmitted probe light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2A:
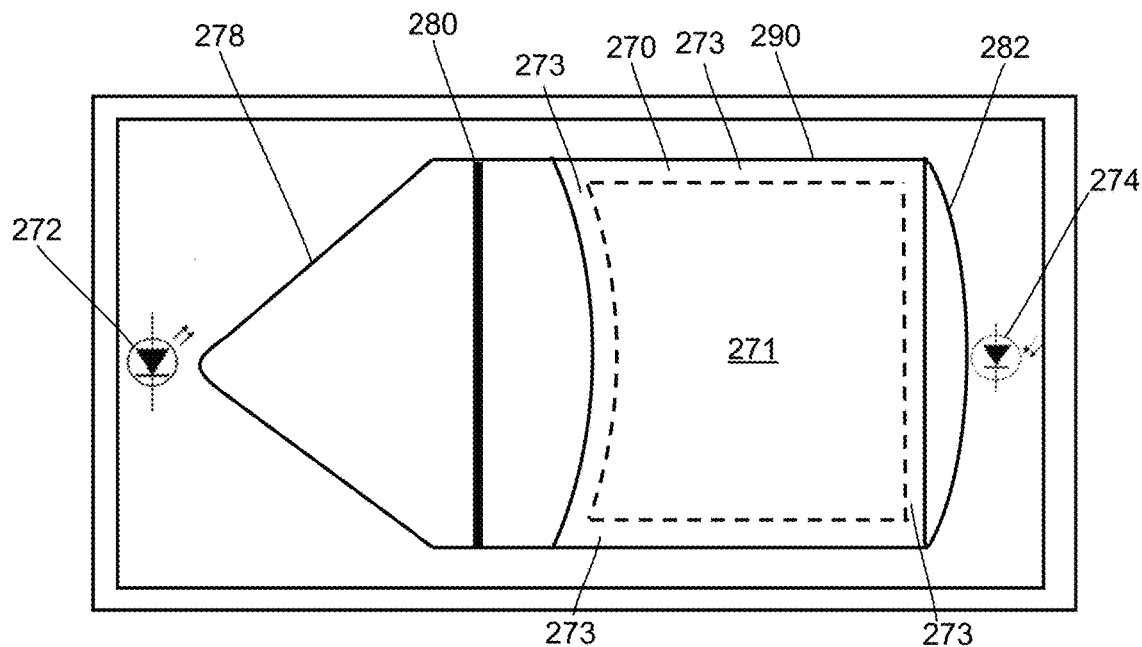
FIG. 2A is a schematic side view of an embodiment of a portion of a magnetometer, according to the invention.

The molecular glue described above can be used to manufacture a gas or vapor cell or to attach optical components (or other components) to a gas or vapor cell. FIG. 2A is an example of one embodiment of a vapor cell 270 with additional optical components integrated together into a structure 290. The vapor cell 270 can be made of any suitable material including, but not limited to, glass, sapphire, silicon, aluminum oxide, or the like or any combination thereof. In at least some embodiments, the molecular glue can be used to attach two or more cell wall substrates together to form the walls 273 of the vapor cell 270. In other embodiments, the vapor cell 270 can be made of single piece of material.

The vapor cell defines a cavity 271 that contains a vapor or vaporizable material, for example, an alkali metal such as lithium, sodium, potassium, rubidium, cerium, or francium. The cavity may also include a buffer gas, quenching gas, or any other suitable material for operation of the magnetometer, or any combination thereof.

The structure 290 can include one or more optical components for laser beam shaping, collimation, and collection that are integrated with, or attached to, the vapor cell 270 to form the structure 290. In some embodiments, the molecular glue described above can be used to attach one or more components to the vapor cell 270.

In the embodiment of FIG. 2A, the structure 290 includes a collimating element 278 (or other beam-shaping element) with, for example, a high conic-constant surface which can collimate the light, a quarter wave plate 280, a vapor cell 270, and a lens element 282. These elements are optical components of the vapor cell 270. Optical components can include, but are not limited to, collimating elements, lens elements, beam-shaping elements, polarizing elements, wave plates, beam splitters, prisms, reflective surfaces, filters, diffusers, gratings, or the like, or any combination thereof. The collimating element 278 and lens element 282 can take shapes other than those illustrated in FIG. 2A. In at least some embodiments, one or more of the collimating element 278, the quarter wave plate 280, or the lens element 282 (or any other optical component(s)) can be attached to the vapor cell 270 or each other using the molecular glue. Light directed from the light source 272 through the alkali metal vapor cell 270 passes through the lens element 282 which concentrates or redirects the light onto the detector 274.

Figure 2B:
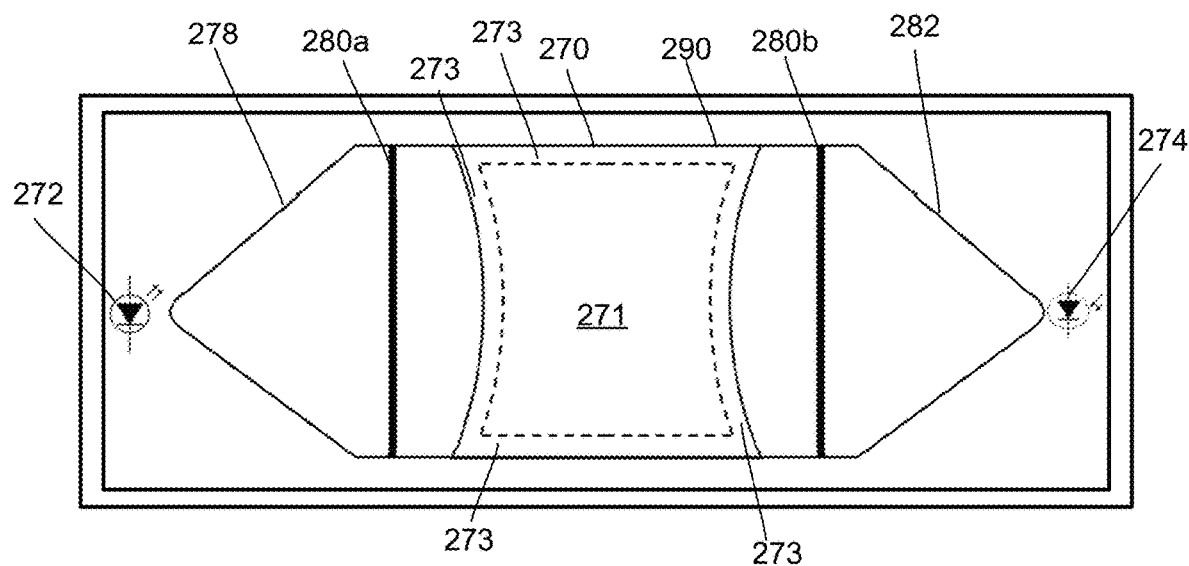
FIG. 2B is a schematic side view of another embodiment of a portion of a magnetometer, according to the invention.

FIG. 2B is another example of an embodiment of a vapor cell 270 with optical components, including a collimating element 278, two quarter wave plates 280a, 280b, and a lens element 282 forming structure 290. These elements are optical components of the vapor cell 270. The structure 290 in FIG. 2B has a symmetric arrangement of elements. In at least some embodiments, one or more of the collimating element 278, the two quarter wave plates 280a, 280b, or the lens element 282 (or any other optical component(s)) can be attached to the vapor cell 270 or each other using the molecular glue.

Figure 1B:
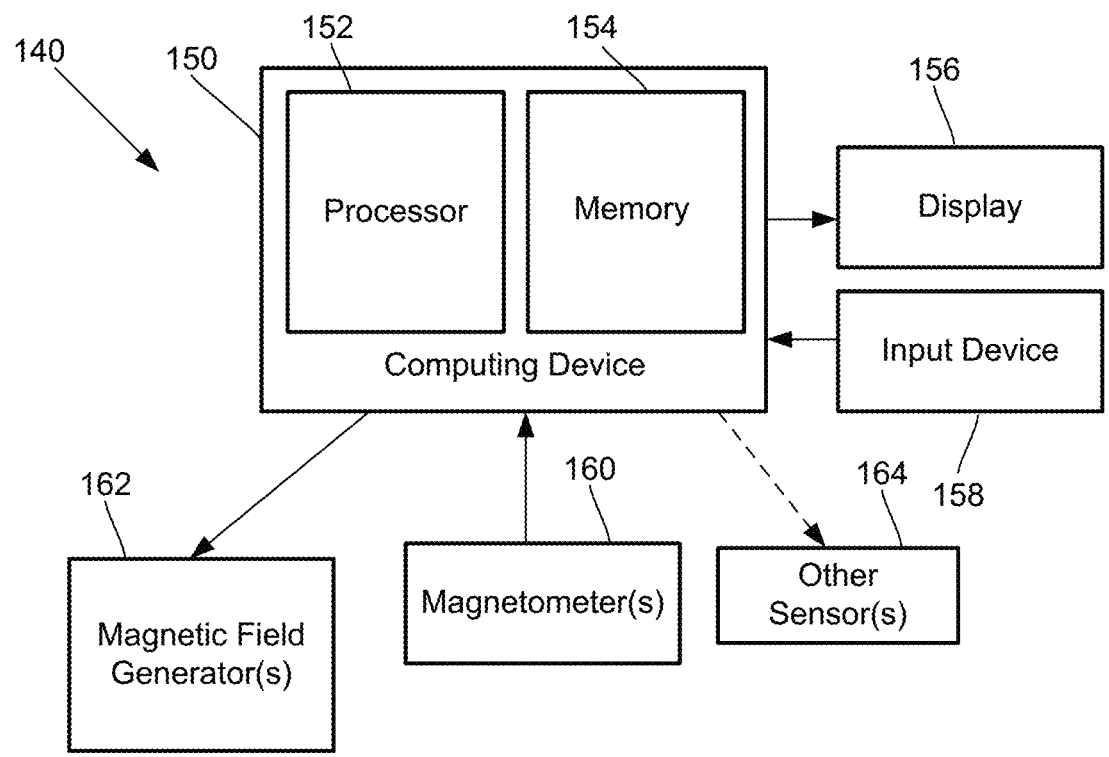
FIG. 1B is a schematic block diagram of one embodiment of a magnetic field measurement system, according to the invention.

A magnetometer, such as magnetometer 160 of FIG. 1A, can be used as part of a magnetic field measurement system. FIG. 1B is a block diagram of components of one embodiment of a magnetic field measurement system 140. The system 140 can include a computing device 150 or any other similar device that includes a processor 152, a memory 154, a display 156, an input device 158, one or more magnetometers 160 (for example, an array of magnetometers) which can be optically pumped magnetometers (OPMs), one or more magnetic field generators 162, and, optionally, one or more other sensors 164 (e.g., non-magnetic field sensors). The system 140 and its use and operation will be described herein with respect to the measurement of neural signals arising from one or more magnetic field sources of interest in the brain of a user as an example. It will be understood, however, that the system can be adapted and used to measure signals from other magnetic field sources of interest including, but not limited to, other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device. The processor 152 is configured to execute instructions stored in the memory 154.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. The optional sensor(s) 164 can include, but are not limited to, one or more position sensors, orientation sensors, accelerometers, image recorders, or the like or any combination thereof.

The one or more magnetometers 160 can be any suitable magnetometer including, but not limited to, any suitable optically pumped magnetometer (e.g., vector magnetometers). Arrays of magnetometers are described in more detail herein. In at least some embodiments, at least one of the one or more magnetometers (or all of the magnetometers) of the system is arranged for operation in a spin exchange relaxation free (SERF) mode.

Figure 3:
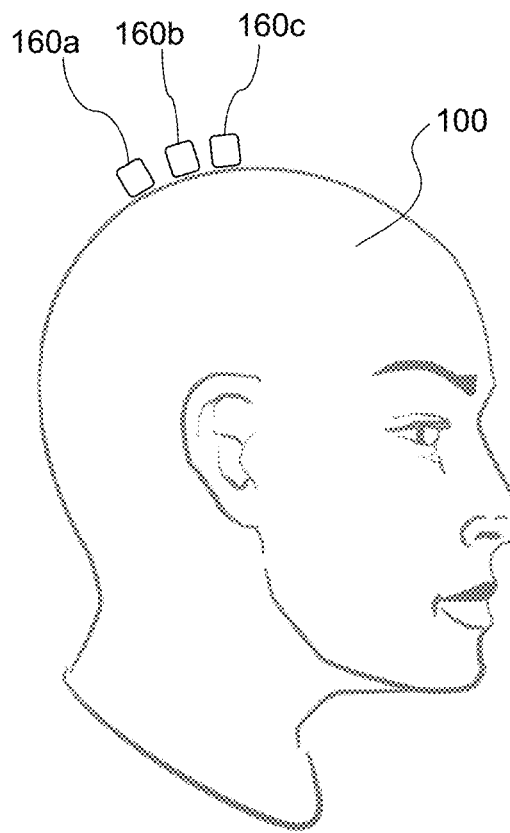
FIG. 3 is a schematic side view of one embodiment of an array of magnetometers for measuring magnetic fields generated in a brain of a user, according to the invention.
Figure 4:
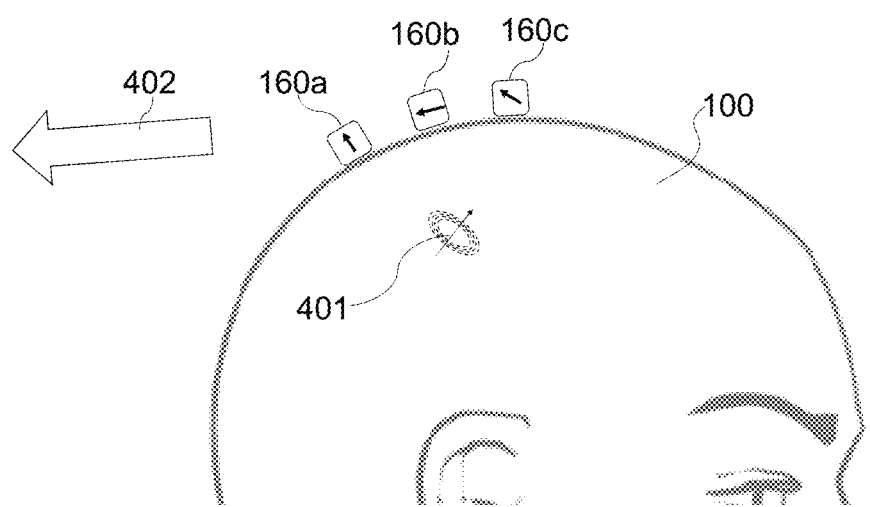
FIG. 4 is a schematic side view of one embodiment of the array of magnetometers of FIG. 3, a signal source in a brain of a user, and a direction of the ambient background magnetic field.

FIG. 3 illustrates one embodiment of a magnetic field measurement system shown with several magnetometers, 160a, 160b, 160c placed on or near a user's head 100 to measure neural activity. FIG. 4 illustrates vector magnetic fields (e.g., signals) that might be generated by the neural activity 401 on each of the magnetometers. For each of the magnetometers 160a, 160b, 106c, the magnetic field vector could be different in both direction and amplitude. The ambient background magnetic field 402 (including, for example, the Earth's magnetic field) is about $10^8$ times larger than magnetic field from the neural activity and is not shown to scale. Examples of magnetic field measurement systems are described in U.S. patent application Ser. Nos. 16/213,980; 16/405,382; 16/418,478; 16/418,500; 16/428,871; 16/456,975; and 16/457,655, and U.S. Provisional Patent Applications Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; and 62/896,929, all of which are incorporated herein by reference in their entireties.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A method for bonding together two substrates, the method comprising:
   providing a molecular glue comprising glue molecules, each of the glue molecules having at least two —O—Si or —O—Al moieties, wherein the glue molecules are selected from Al(OR)$_2$—O-L-O—Al(OR)$_2$ or Si(OR)$_3$—O-L-O—Si(OR)$_3$, wherein each R is independently hydrogen or C$_1$ to C$_8$ branched or unbranched alkyl and L is a linker group selected from C$_1$ to C$_{30}$ branched or unbranched alkylene or C$_6$ to C$_{30}$ cycloalkylene or C$_6$ to C$_{30}$ arylene;
   reacting a surface of a first substrate with the molecular glue to attach the glue molecules to the surface of the first substrate by at least one of the —O—Si or —O—Al moieties; and
   reacting a surface of a second substrate with the molecular glue to attach the glue molecules to the surface of the second substrate by at least another one of the —O—Si or —O—Al moieties.

2. The method of claim 1, wherein each R is independently —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, or —C(CH$_3$)$_3$.

3. The method of claim 1, wherein L is —(CH$_2$)x- or benzylene, wherein x is an integer in the range of 1 to 15.

4. The method of claim 1, wherein at least one of the first substrate or the second substrate is an inorganic substrate.

5. The method of claim 4, wherein at least one of the first substrate or the second substrate is a silicon, glass, aluminum oxide, corundum, ruby, or sapphire substrate.

6. The method of claim 5, wherein both the first and second substrates are silicon, glass, aluminum oxide, corundum, ruby, or sapphire substrates.

7. The method of claim 1, wherein reacting the surface of the first substrate with the molecular glue comprises disposing the molecular glue on the surface and applying heat or pressure or both heat and pressure to react the molecular glue with the surface.

8. The method of claim 1, wherein reacting the surface of the first substrate with the molecular glue and reacting the surface of the second substrate with the molecular glue comprise disposing the molecular glue on the surface of the first substrate, positioning the second substrate on the first substrate, and applying heat or pressure or both heat and pressure to react the molecular glue with the surfaces of the first and second substrates.

9. A method for forming a vapor cell, the method comprising:
   providing a molecular glue comprising glue molecules, each of the glue molecules having at least two —O—Si or —O—Al moieties;
   reacting a surface of a first vapor cell substrate with the molecular glue to attach the glue molecules to the surface of the first vapor cell substrate by at least one of the —O—Si or —O—Al moieties; and
   reacting a surface of a second vapor cell substrate with the molecular glue to attach the glue molecules to the surface of the second vapor cell substrate by at least another one of the —O—Si or —O—Al moieties.

10. The method of claim 9, wherein the first vapor cell substrate is a first cell wall and the second vapor cell substrate is a second cell wall.

11. The method of claim 9, wherein the first vapor cell substrate is a cell wall and the second vapor cell substrate is an optical component of the vapor cell.

12. The method of claim 9, wherein the first vapor cell substrate is a first optical component and the second vapor cell substrate is a second optical component.

13. The method of claim 12, wherein the first optical component is selected from a collimating element, a quarter wave plate, or a lens element.

14. A vapor cell, comprising:
   a first substrate forming either a first cell wall or a first optical component;
   a second substrate forming either a second cell wall or a second optical component; and
   a molecular glue disposed between the first and second substrates and bonding the first and second substrates together, wherein a molecular glue comprises glue molecules, each of the glue molecules comprising at least two —O—Si or —O—Al moieties, wherein the —O—Si or —O—Al moieties form silicate or aluminate bonds to the first and second substrates.

15. The vapor cell of claim 14, wherein the glue molecules are selected from Al(OR)$_3$ or Si(OR)$_4$, wherein each R is independently hydrogen or C$_1$ to C$_8$ branched or unbranched alkyl.

16. The vapor cell of claim 14, wherein the glue molecules are selected from Al(OR)$_2$—O-L-O—Al(OR)$_2$ or Si(OR)$_3$—O-L-O—Si(OR)$_3$, wherein each R is independently hydrogen or C$_1$ to C$_8$ branched or unbranched alkyl and L is a linker group selected from C$_1$ to C$_{30}$ branched or unbranched alkylene or C$_6$ to C$_{30}$ cycloalkylene or C$_6$ to C$_{30}$ arylene.

17. The method of claim 9, wherein the glue molecules are selected from Al(OR)$_3$ or Si(OR)$_4$, wherein each R is independently hydrogen or C$_1$ to C$_8$ branched or unbranched alkyl.

18. The method of claim 17, wherein each R is independently —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$)CH$_2$CH$_3$, or —C(CH$_3$)$_3$.

19. The method of claim 9, wherein the glue molecules are selected from Al(OR)$_2$—O-L-O—Al(OR)$_2$ or Si(OR)$_3$—O-L-O—Si(OR)$_3$, wherein each R is independently hydrogen or $C_1$ to $C_8$ branched or unbranched alkyl and L is a linker group selected from $C_1$ to $C_{30}$ branched or unbranched alkylene or $C_6$ to $C_{30}$ cycloalkylene or $C_6$ to $C_{30}$ arylene.

20. The method of claim 9, wherein both the first and second vapor cell substrates are silicon, glass, aluminum oxide, corundum, ruby, or sapphire substrates.

* * * * *